United States Patent

Araki et al.

[11] Patent Number: 5,420,094
[45] Date of Patent: May 30, 1995

[54] RECORDING MATERIAL

[75] Inventors: Katsumi Araki; Masanobu Takashima; Masato Satomura; Shunsaku Higashi, all of Shizuoka, Japan

[73] Assignee: Fuji Photo Film Co., Ltd., Kanagawa, Japan

[21] Appl. No.: 51,325

[22] Filed: Apr. 23, 1993

[30] Foreign Application Priority Data

Apr. 24, 1992 [JP] Japan .................. 4-106640
Apr. 28, 1992 [JP] Japan .................. 4-109831

[51] Int. Cl.$^6$ ............... B41M 5/155; B41M 5/28
[52] U.S. Cl. .................... 503/216; 427/151; 503/225
[58] Field of Search ............ 427/150, 151; 503/216, 503/225; 560/72

[56] References Cited

U.S. PATENT DOCUMENTS

| | | | |
|---|---|---|---|
| 4,306,055 | 12/1981 | Baron et al. | 528/171 |
| 4,446,209 | 5/1984 | Iwakura et al. | 346/216 |
| 4,583,104 | 4/1986 | Iwakura et al. | 346/216 |

FOREIGN PATENT DOCUMENTS

| | | | |
|---|---|---|---|
| 0082384 | 6/1983 | European Pat. Off. | 428/411.1 |
| 1514802 | 3/1967 | France | 428/411.1 |
| 1178489 | 7/1989 | Japan | 503/216 |

OTHER PUBLICATIONS

Patent Abstract of Japan, vol. 13, No. 327, Jul. 24, 1989, JPA 01 110 185 (with copy of patent).
Patent Abstract of Japan, vol. 198, No. 198, Apr. 19, 1993, JPA 04 344 286 (with copy of patent).

*Primary Examiner*—B. Hamilton Hess
*Attorney, Agent, or Firm*—Sughrue, Mion, Zinn, Macpeak & Seas

[57] ABSTRACT

Disclosed is a novel recording material comprising an electron-providing colorless dye and an electron-accepting compound. The electron-accepting compound is represented by the following formula (1):

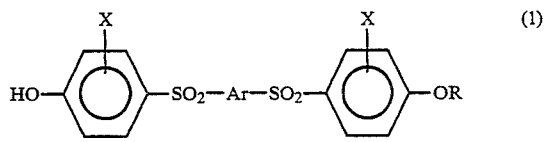

wherein X represents a hydrogen atom, a halogen atom, a hydroxyl group, a carboxyl group, an alkoxycarbonyl group, an alkyl group, an alkoxy group, an allyl group, an aryl group, an aralkyl group or a cycloalkyl group; Ar represents an arylene group containing two to five benzene rings, an arylene group condensed with two to five benzene rings or a bisarylene group in which arylene groups are connected to each other via a divalent group; and R represents a hydrogen atom, an alkyl group, an aralkyl group or an aryloxyalkyl group. The invention also relates to the compounds of formula (1).

6 Claims, No Drawings

RECORDING MATERIAL

FIELD OF THE INVENTION

The present invention relates to a recording material comprising an electron-providing colorless dye and an electron-accepting compound, such as a pressure-sensitive recording material or a heat-sensitive recording material. More particularly, it relates to such a recording material which exhibits excellent color density, excellent color sensitivity, and excellent storage stability of nonimage and image portions.

The present invention further relates to electron-accepting compounds useful in pressure-sensitive recording material, heat-sensitive recording material, etc.

BACKGROUND OF THE INVENTION

A recording material comprising an electron-providing colorless dye and an electron-accepting compound is known for use as pressure-sensitive paper, heat-sensitive paper, photosensitive pressure-sensitive paper, electric heat-sensitive recording paper, heat-sensitive transfer paper, etc. These recording materials are further described in British Patent 2,140,449, U.S. Pat. Nos. 4,480,052, and 4,436,920, JP-B-60-23992 (The term "JP-B" as used herein means an "examined Japanese patent publication"), and JP-A-57-179836, JP-A-60-123556, and JP-A-60-123557 (The term "JP-A" as used herein means an "unexamined published Japanese patent application").

In the field of recording materials, extensive study has recently been made to improve their properties such as (1) color density and sensitivity and (2) storage stability of nonimage and image portions.

Electron-accepting compounds to be used in combination with electron-providing colorless dyes include various compounds such as bisphenol A, p-hydroxybenzoic ester and bis-(4-hydroxyphenyl)sulfone. However, all these compounds have disadvantage in color density, color sensitivity or storage stability (e.g., weathering resistance, chemical resistance, plasticizer resistance). For example, bis-(3-phenyl-4-hydroxyphenyl)sulfone, when incorporated into a heat-sensitive recording material, is poor in preservability of the nonimage portion as demonstrated by fog on the background with marking ink, fluorescent ink, etc. Further, 4-isopropoxy-4'-hydroxydiphenylsulfone, when incorporated into a heat-sensitive recording paper, exhibits a high color density and sensitivity, but leaves much to be desired in chemical resistance as demonstrated by coloring on the background with marking ink, fluorescent ink, etc. and fading of typed images.

The inventors have found that specific compounds are useful for the improvement of these properties.

SUMMARY OF THE INVENTION

It is therefore an object of the present invention to provide a recording material which exhibits excellent color density, excellent color sensitivity and excellent storage stability (e.g., weathering resistance, chemical resistance, plasticizer resistance) of nonimage and image portions, as well as meeting other requirements.

The aforementioned objects of the present invention will become more apparent from the following detailed description and examples.

These and other objects of the present invention are accomplished with a recording material comprising an electron-providing colorless dye and an electron-accepting compound. The electron-accepting compound is represented by the following formula (1):

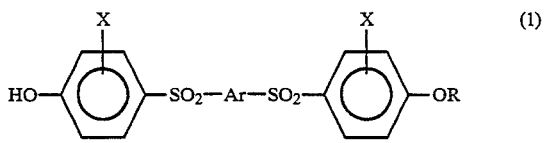

wherein X represents a hydrogen atom, a halogen atom, a hydroxyl group, a carboxyl group, an alkoxycarbonyl group, an alkyl group, an alkoxy group, an allyl group, an aryl group, an aralkyl group or a cycloalkyl group; Ar represents an arylene group containing two to five benzene rings, an arylene group condensed with two to five benzene rings or a bisarylene group in which arylene groups are connected to each other via a divalent group; and R represents a hydrogen atom, an alkyl group, an aralkyl group or an aryloxyalkyl group.

DETAILED DESCRIPTION OF THE INVENTION

The compound represented by formula (1) is preferably one represented by the following formula (2):

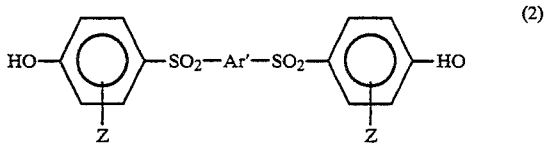

wherein Ar' is an arylene group containing two to five benzene rings, an arylene group condensed with two to five benzene rings, or a bisarylene group in which arylene groups are connected to each other via a divalent group; and Z represents a hydrogen atom, a halogen atom, an alkyl group, an aralkyl group, an allyl group, an aryl group, a hydroxyl group, a carboxyl group, an alkoxy group or an alkoxycarbonyl group.

The compound represented by formula (2) is preferably a diphenylether derivative represented by the following formula (3):

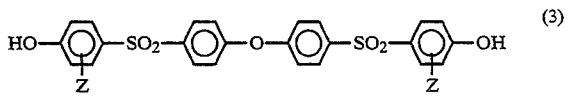

wherein Z is as defined above.

The compound represented by formula (3) is preferably a diphenylether derivative wherein the substituent Z is a hydrogen atom, a halogen atom, a $C_{1-10}$ alkyl group, a $C_{6-10}$ aralkyl group, a $C_{6-10}$ aryl group or an allyl group.

In formula (1), the group represented by X is preferably a hydrogen atom, a hydroxyl group, a carboxyl group, a $C_{1-7}$ alkoxycarbonyl group, a fluorine atom, a chlorine atom, a bromine atom, a $C_{1-5}$ alkyl group, a $C_{1-5}$ alkoxy group, an allyl group, a $C_{7-10}$ aryl group, a $C_{7-10}$ aralkyl group or a $C_{5-7}$ cycloalkyl group.

In formula (1), the group represented by Ar is preferably a condensed ring or a divalent group represented by the following formula (4):

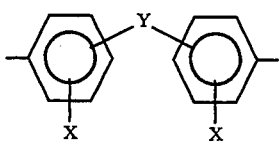
(4)

wherein Y represents a single bond, $C_{1-10}$ alkylene group, phenylene group, oxygen atom, sulfur atom, carbonyl group or sulfone group; and X is as defined above.

In formula (1), the group represented by R is preferably a hydrogen atom, $C_{1-10}$ alkyl group, $C_{7-20}$ aralkyl group or $C_{8-20}$ aryloxyalkyl group.

In formula (1), particularly preferred examples of the group represented by X include hydrogen atom, hydroxyl group, carboxyl group, methoxycarbonyl group, ethoxycarbonyl group, normal propoxycarbonyl group, isopropoxycarbonyl group, normal butylcarbonyl group, isobutyloxycarbonyl group, chlorine atom, methyl group, ethyl group, normal propyl group, isopropyl group, tertiary butyl group, secondary butyl group, methoxy group, ethoxy group, allyl group, phenyl group, benzyl group, cyclohexyl group, α-phenylpropyl group, and α-phenylallyl group.

In formula (1), particularly preferred examples of the group represented by Ar include 2,7-naphthylene group, 1,5-napthylene group, anthracenylene group, and group represented by the following formula (5):

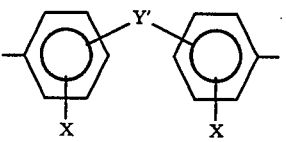
(5)

wherein Y' represents a single bond, methylene group, ethylene group, isopropylidene group, butylene group, phenylene group, oxygen atom, sulfur atom, carbonyl group or sulfone group; and X is as defined above. Y' is preferably in a position para to sulfonyl group.

In formula (1), particularly preferred examples of the group represented by R include hydrogen atom, methyl group, normal propyl group, isopropyl group, normal butyl group, tertiary butyl group, secondary butyl group, isobutyl group, normal amyl group, isoamyl group, normal hexyl group, normal octyl group, benzyl group, paramethylbenzyl group, paraethylbenzyl group, paranormal propylbenzyl group, paraisopropylbenzyl group, methoxybenzyl group, chlorobenzyl group, phenethyl group, phenylpropyl group, naphthylmethyl group, phenoxyethyl group, methoxyphenoxyethyl group, chlorophenoxyethyl group, methylphenoxyethyl group, 1-methyl-2-phenoxyethyl group, 1-methyl-2-(methoxyphenoxy)ethyl group, 1-methyl-2-(methylphenoxy)ethyl group, 2-napthoxyethyl group, 1-napthoxyethyl group, and 1-methyl-2-(2-napthoxy)ethyl group.

The group represented by Z is preferably a hydrogen atom, halogen atom, $C_{1-6}$ alkyl group, $C_{7-10}$ aralkyl group, allyl group or $C_{6-10}$ aryl group. Particularly preferred examples of the group represented by Z include hydrogen atom, chlorine atom, bromine atom, methyl group, ethyl group, normal propyl group, isopropyl group, secondary butyl group, tertiary butyl group, benzyl group, allyl group, phenyl group, and α-phenyallyl group.

Specific examples of the compound represented by formula (1) are shown below, but the present invention should not be construed as being limited thereto. The following structural formulae include their hydrates:

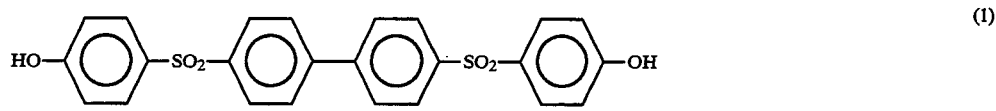
(1)

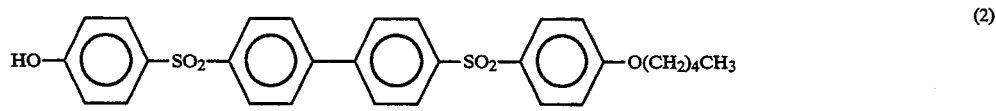
(2)

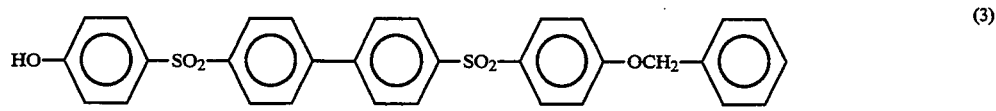
(3)

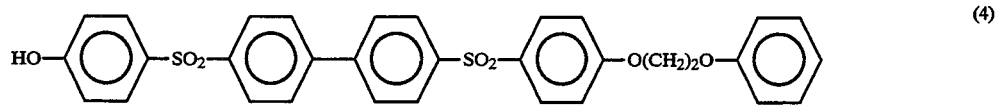
(4)

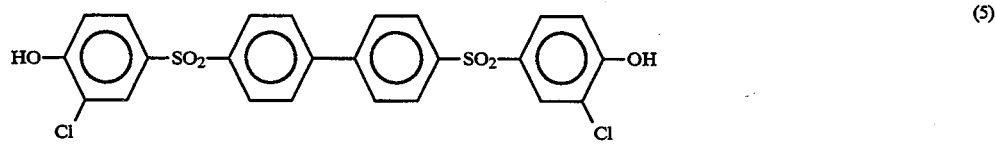
(5)

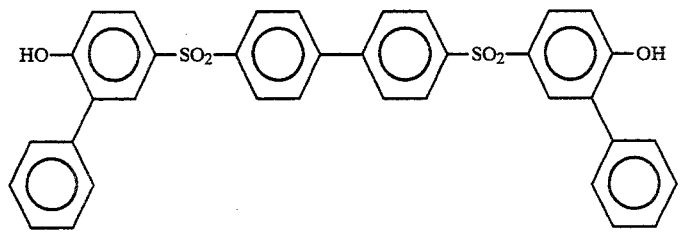
(6)
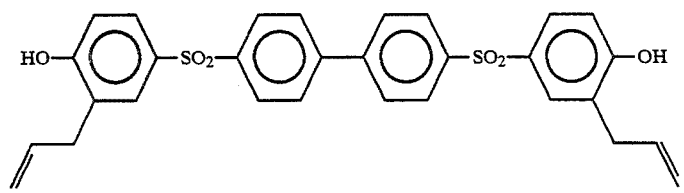
(7)
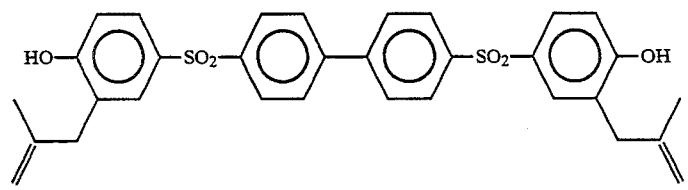
(8)
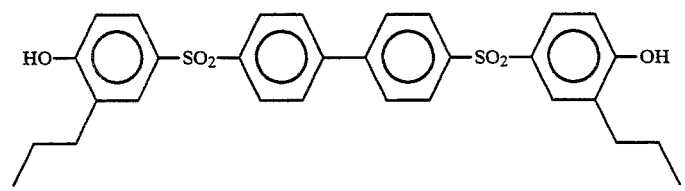
(9)
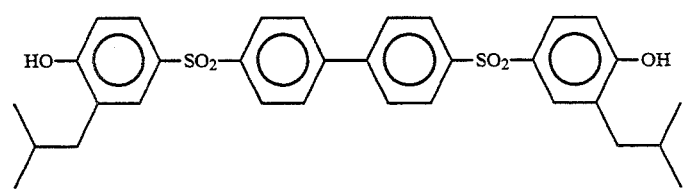
(10)
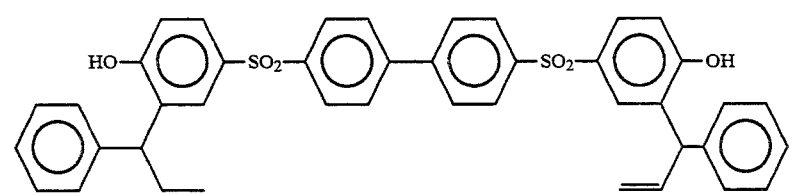
(11)
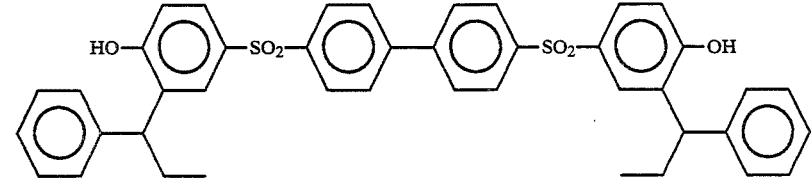
(12)
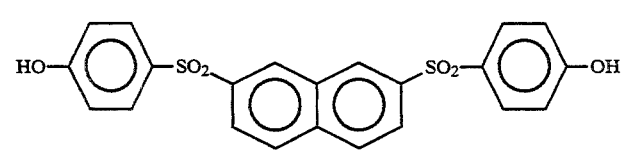
(13)

-continued
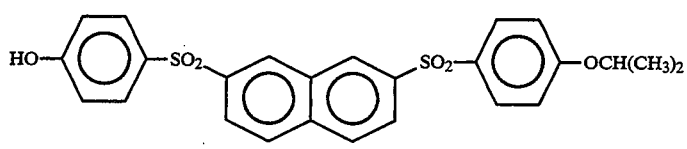 (14)
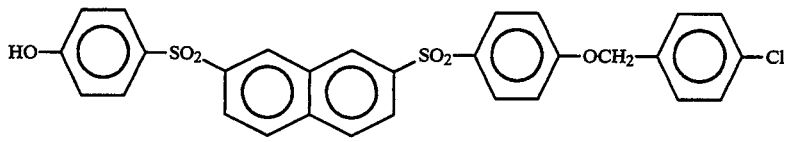 (15)
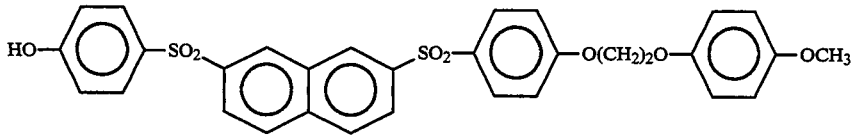 (16)
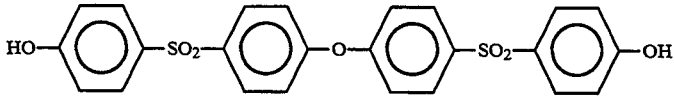 (17)
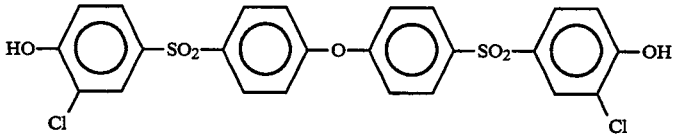 (18)
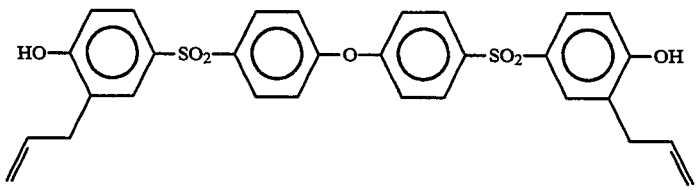 (19)
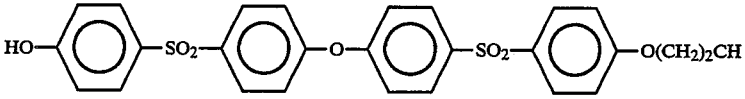 (20)
 (21)
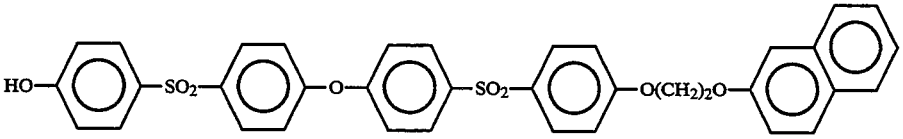 (22)
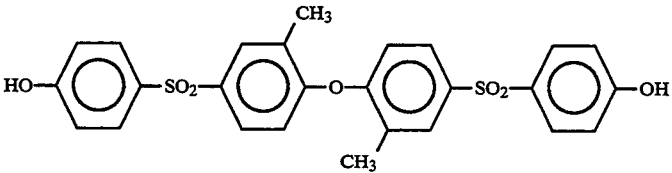 (23)
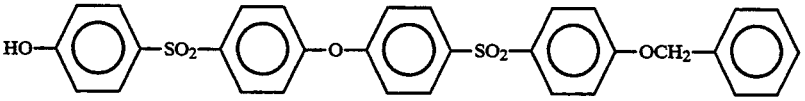 (24)

-continued
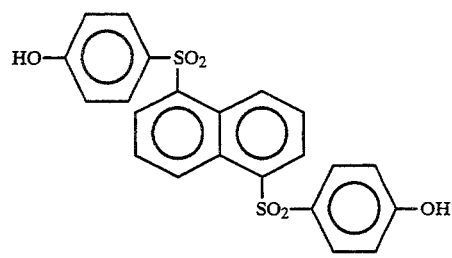
(25)
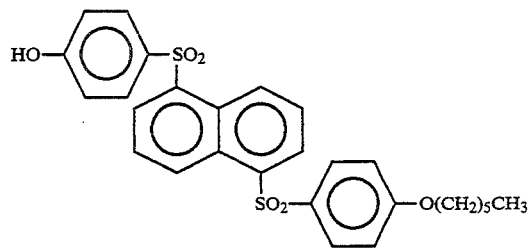
(26)
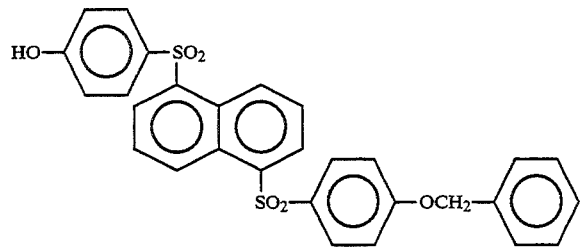
(27)
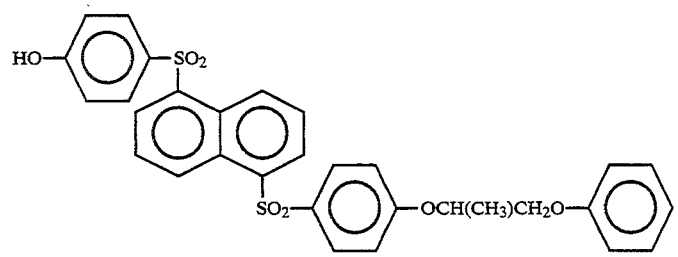
(28)
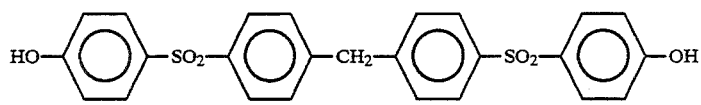
(29)
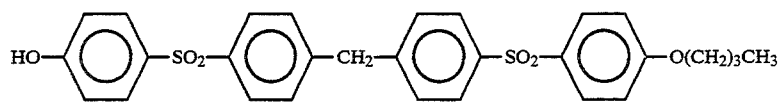
(30)
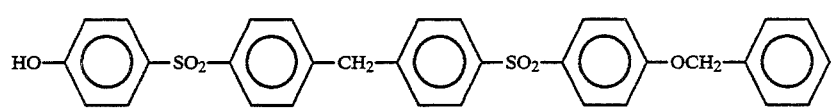
(31)
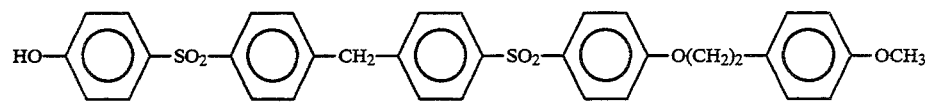
(32)

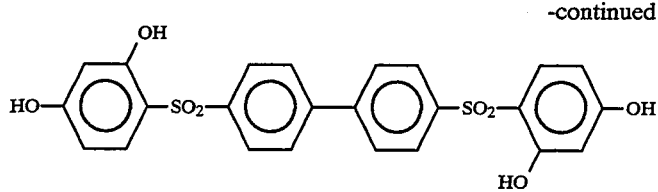
(33)
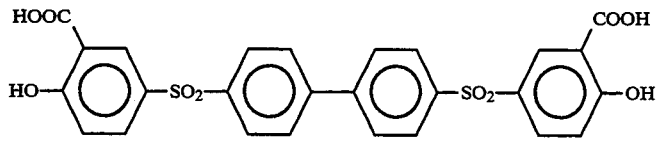
(34)
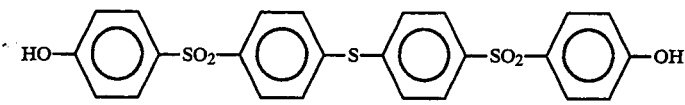
(35)
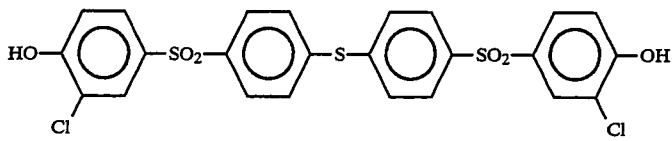
(36)
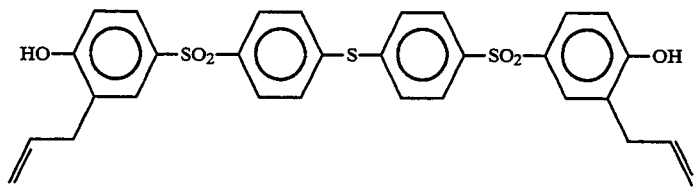
(37)
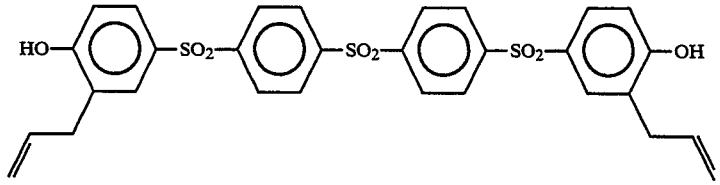
(38)
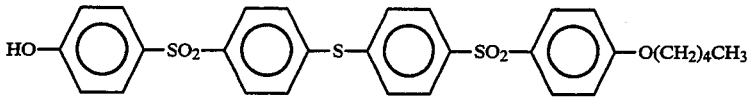
(39)
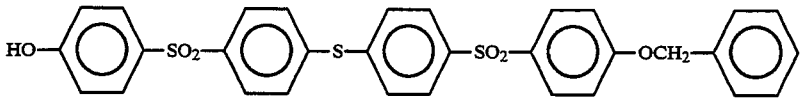
(40)
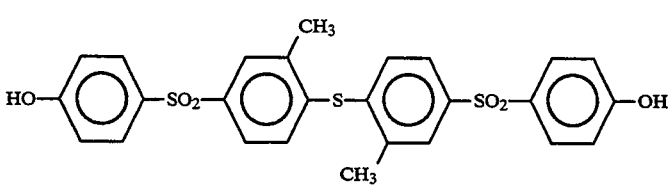
(41)
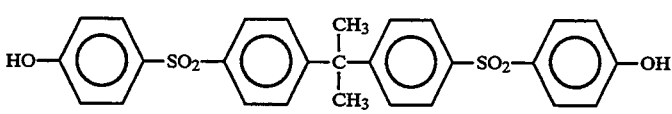
(42)
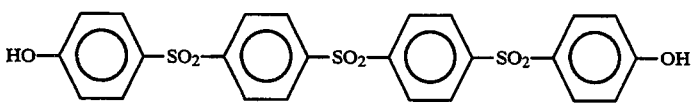
(43)

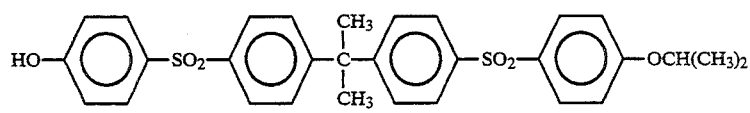
(44)
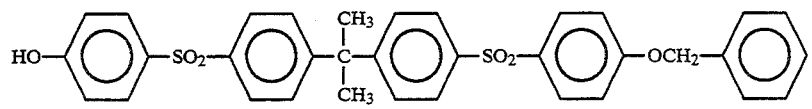
(45)
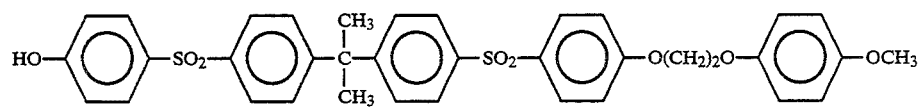
(46)
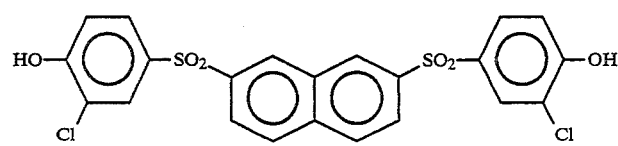
(47)
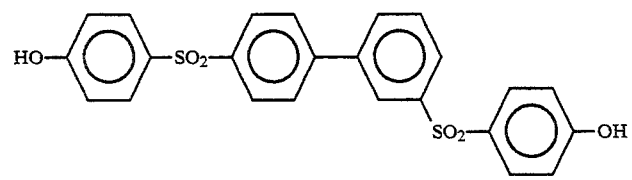
(48)
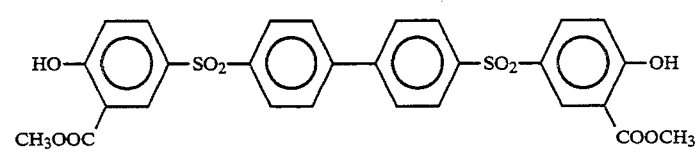
(49)
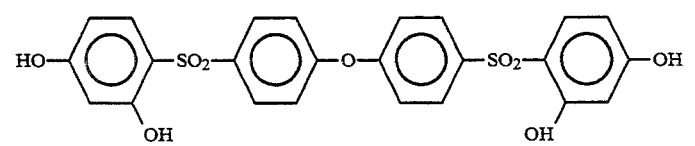
(50)
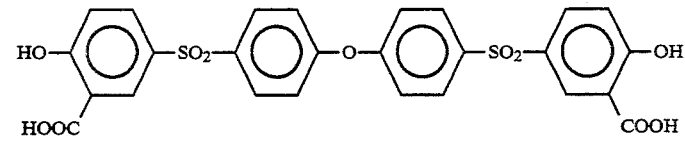
(51)
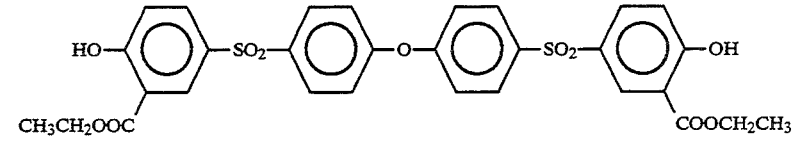
(52)
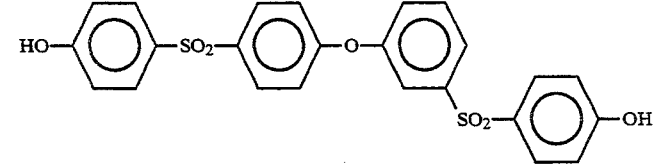
(53)

-continued

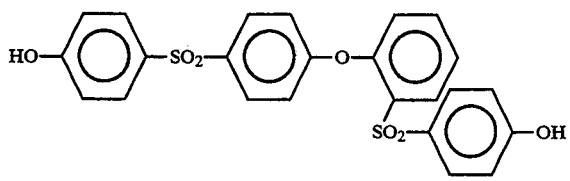
(54)

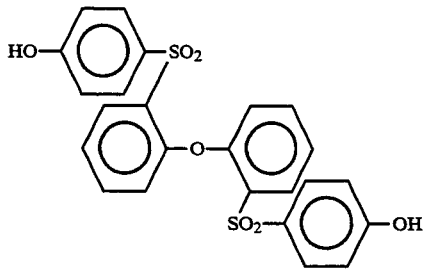
(55)

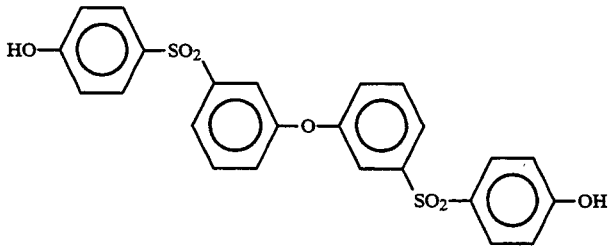
(56)

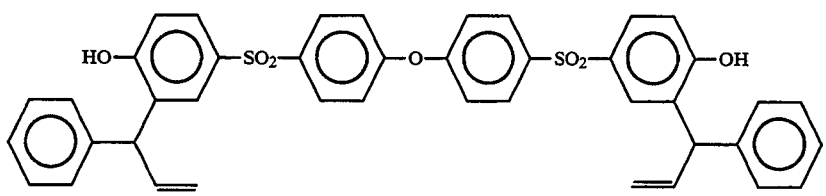
(57)

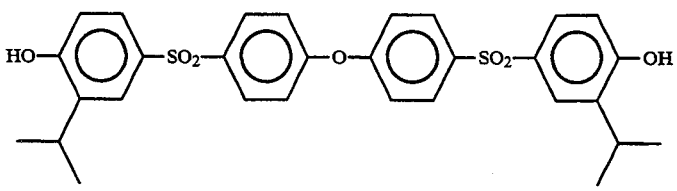
(58)

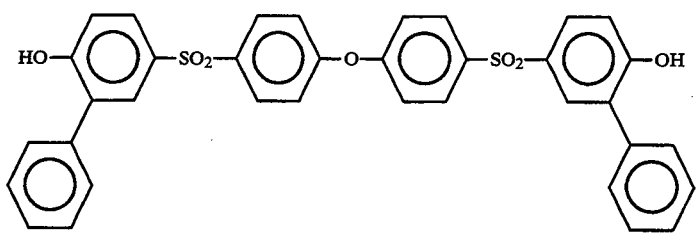
(59)

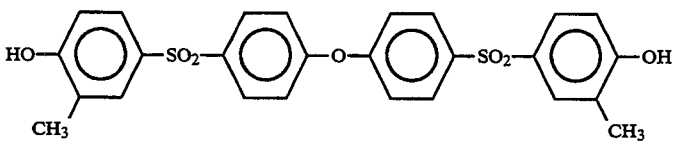
(60)

The melting point of the compounds represented by formula (1) can be controlled by incorporating water an organic solvent in the crystal. For example, Exemplary Compound (17) exhibits a melting point of 195° to 196° C. if it is free of water or organic solvent. However, if it contains water in its crystal, it exhibits a melting point of 100° C. When a heat-sensitive recording material comprises such a compound, an image formed therefrom exhibits an excellent chemical resistance.

The electron-providing colorless dyes in the present invention include various known triphenylmethane phthalide compounds, fluoran compounds, phenothiazine compounds, indolyl phthalide compounds, leucoauramine compounds, rhodamine lactam compounds, triphenylmethane compounds, triazene compounds, spiropyrane compounds, and fluorene compounds.

Specific examples of the phthalides are disclosed in U.S. Pat. Nos. Re. 23,024, 3,491,111, 3,491,112, 3,491,116, and 3,509,174. Specific examples of the fluorans are disclosed in U.S. Pat. Nos. 3,624,107, 3,627,787, 3,641,011, 3,462,828, 3,681,390, 3,920,510, and 3,959,571. Specific examples of the spirodipyranes are disclosed in U.S. Pat. No. 3,971,808. Specific examples of the pyridine and pyrazine compounds are disclosed in U.S. Pat. Nos. 3,775,424, 3,853,869, and 4,264,318. Specific examples of the fluorene compounds are disclosed in JP-A-63-94878.

Examples of these electron-providing colorless dyes are given below, but the present invention should not be construed as being limited thereto:

3,3-bis(p-dimethylaminophenyl)-6-dimethylaminophthalide, 3,3-bis(p-dimethylaminophenyl)phthalide, 3-( p-dimethylaminophenyl)-3-(1,2-dimethylindol-3-il)phthalide, 3-(p-dimethylaminophenyl)-3-(2-methylindol-3-il)phthalide, 3,3-bis(1,2-dimethylindol-3-il)-5-dimethylaminophthalide, 3,3-bis(1,2-dimethylindol-3-il)-6-dimethylaminophthalide, 3,3-bis(9-ethylcarbazole-3-il)-6-dimethylaminophthalide;

triarylmethane dyes such as 3-(2-ethoxy-4-diethylaminophenyl)-3-(1-normaloctyl-2-methylindol-3-il)phthalide, 3-(2-ethoxy-4-diethylaminophenyl)-3-(1-normaloctyl-2-methylindol-3-il)-4-azaphthalide, 3,3-bis(1-normaloctyl-2-methylindol-3-il)phthalide, 3,3-bis(2-phenylindol-3-il)-6-dimethylaminophthalide and 3-p-dimethylaminophenyl-3-(1-methylpyrrole-3-il)-6-dimethylaminophthalide, diphenylmethane dyes such as 4,4'-bis-dimethylaminobenzhydrylbenzylether, N-halophenyl-leucoauramine and N-2,4,5-trichlorophenyl-leucoauramine, and thiadine dyes such as benzoyl leucomethylene blue and p-nitrobenzoyl leucomethylene blue;

spiro dyes such as 3-methyl-spiro-dinaphthopyrane, 3-ethyl-spiro-dinaphthopyrane, 3-phenyl-spiro-dinaphthopyrane, 3-benzyl-spiro-dinaphthopyrane, 3-methyl-naphtho(6'-methoxybenzo)spiropyrane and tertiarypropyl-spiro-dibenzopyrane, and lactam dyes such as rhodamine-B-anilinolactam, rhodamine(p-nitroanilino)lactam and rhodamine(o-chloroanilino)lactam;

3-dimethylamino-7-methoxyfluoran, 3-methoxy-6-diethylaminofluoran, 3-diethylamino-7-methoxyfluoran, 3-diethylamino-7-chlorofluoran, 3-diethylamino-6-methyl-7-chlorofluoran, 3-diethylamino-6,7-dimethylfluoran, 3-(N-ethyl-p-toluidino)-7-methylfluoran, 3-diethylamino-7-N-acetyl-N-methylaminofluoran, 3-diethylamino-7-N-methylaminofluoran;

3-diethylamino-7-dibenzylaminofluoran, 3-diethylamino-7-N-methyl-N-benzylaminofluoran, 3-diethylamino-7-N-chloroethyl-N-methylaminofluoran, 3-diethylamino-7-N-diethylaminofluoran, 2-phenylamino-3-methyl-6-(N-ethyl-p-toluidino)-fluoran, 2-(p-toluidino)-3-methyl-6-(N-ethyl-p-toluidino)fluoran, 2-anilino-3-methyl-6-diethylaminofluoran;

2-anilino-3-methyl-6-dibutylaminofluoran, 2-(2-carbomethoxy-phenylamino)-6-diethylaminofluoran, 2-anilino-3-methyl-6-(N-cyclohexyl-N-isoamylamino)fluoran, 2-anilino-3-methyl-6-(N-cyclohexyl-N-methylamino)amylfluoran, 2-anilino-3-pyrrolidinofluoran, 2-anilino-3-methyl-6-piperidinoaminofluoran, 3-diethylamino-6-methyl-7-xylidinofluoran;

2-(o-chlorophenylamino)-6-diethylaminofluoran, 2-(o-chlorophenylamino)-6-dibutylaminofluoran, 2-anilino-3-methyl-6-(N-ethyl-N-tetrahydrofurfurylamino)fluoran, 2-anilino-3-methyl-6-(N-methyl-N-n-propylamino)fluoran, 2-anilino-3-methyl-6-(N-ethyl-N-isobutylamino)fluoran; and fluoran dyes such as 2-anilino-3-methyl-6-(N-methyl-N-n-hexylamino)fluoran, 2-anilino-3-methyl-6-(N-ethyl-N-n-hexylamino)fluoran, 2-anilino-3-methyl-6-(N-ethyl-N-cyclopentylamino)fluoran, 2-anilino-3-methyl-6-N-ethyl-N-[3-(p-ethylphenoxy)propyl]aminofluoran, 2-anilino-3-methyl-6-N-propyl-N-[3-(p-methoxyphenoxy)propyl]aminofluoran, 2-anilino-3-methyl-6-N-propyl-N-3-ethoxypropylaminofluoran and 2-anilino-3-methyl-6-N-ethyl-N-3-ethoxypropylaminofluoran.

The electron-providing colorless dyes to be used in the present invention are not limited to these dyes. Further, two or more of these dyes may be optionally used in combination. These electron-providing colorless dyes may be incorporated in microcapsules.

The electron-accepting compound of the present invention may be used in combination with known phenol derivatives, salicylic acid derivatives, metallic salts of aromatic carboxylic acids, acidic clay, bentonite, novolak resins, metal-treated novolak resins, metallic complexes, etc.

Examples of the above-described combinations are disclosed in JP-B-40-9309, and JP-B-45-14039, and JP-A-56-140483, JP-A-48-51510, JP-A-57-210886, JP-A-58-87089, JP-A-59-11286, JP-A-60-76795, and JP-A-61-95988.

Examples of the compounds to be used in combination with the electron-accepting compounds include bisphenol A, 2,2-bis(3-methyl-4-hydroxyphenyl)-propane, 2,2-bis(4-hydroxyphenyl)heptane, 1,1-bis(4-hydroxyphenyl)butane, 1,1-bis(4-hydroxyphenyl)-2-ethyl-hexane, 1,1-bis(3-chloro-4-hydroxyphenyl)-2-ethylbutane, bis(3-allyl-4-hydroxyphenyl)sulfone, 1,7-bis(4-hydroxyphenylthio)-3,5-dioxaheptane, (4-hydroxyphenyl)-(4-isopropoxyphenyl)sulfone, 4-hydroxybenzoic benzyl ester, 2,4-dihydroxybenzoate-$\beta$-phenoxyethyl ester, 2,4-dihydroxybenzoate-$\alpha$-methyl-$\beta$-(3-methoxyphenoxy)ethyl ester, 1,3-bis(4-hydroxyphenyl)propane, 2-(2,4-dihydroxyphenyl)-2-phenylpropane, and zinc 3,5-bis($\alpha$-methylbenzyl)salicylate.

When the recording material of the present invention is used as a heat-sensitive paper, it may be in the form described in JP-A-62-114989, and JP-A-1-87291. Specifically, the electron-providing colorless dye and electron-accepting compound are ground to a grain diameter of 10 $\mu$m or less, preferably 3 $\mu$m or less, and dispersed in a dispersant. This dispersant may normally be an aqueous solution of a water-soluble high molecular compound having a concentration of 0.5 to 10%. The dispersion may be accomplished by means of a ball mill, sand mill, horizontal mill, attritor, colloidal mill or the like.

The weight ratio of the electron-providing colorless dye to the electron-accepting compound is 1:20 to 1:1, preferably 1:10 to 1:1, more preferably 1:5 to 2:3.

In order to enhance the heat response of the recording material, a heat-fusible material may be incorporated into the heat-sensitive coloring layer. Typical examples of such a heat-fusible material include an aromatic ether, an aromatic thioether, an aromatic ester, an aliphatic amide, and an aliphatic ureide.

Examples of these heat-fusible materials are disclosed in JP-A-58-57989, JP-A-58-87094, JP-A-61-58789, JP-A-62-109681, JP-A-62-132674, JP-A-63-151478, and JP-A-63-235961, and Japanese Patent Application Nos. 1-4447 and 1-37070.

Specific examples of such heat-fusible materials include phenethyl biphenyl ether, benzyloxy naphthalene, benzyl biphenyl, 1,2-diphenoxyethane, 1,2-di-m-tollyloxyethane, 1-phenoxy-2-p-methoxyphenoxyethane, 1-p-methoxyphenoxy-2-o-chlorophenoxyethane, 1,2-di-p-fluorophenoxyethane, 1,3-di-p-methoxyphenoxypropane, 1,2-di-p-methoxyphenoxypropane, 1-phenoxy-2-p-methoxyphenoxypropane, 1-p-methoxyphenoxyethoxy-2-p-methoxyphenoxyethane, 1,2-di-p-methoxyphenylthioethane, p-methoxybenzyloxytollylmethane, (4-methoxybenzyloxy)-(3-methyl-4-chlorophenyl)methane, and p-chlorobenzyloxy-p-ethoxyphenylmethane.

Such a heat-fusible material may be finely dispersed simultaneously with the electron-providing colorless dye or the electron-accepting compound before use. The amount of the heat-fusible material added is preferably from 20% to 300% by weight, particularly 40% to 150% by weight, based on the weight of the electron-accepting compound.

The coating solution thus obtained may optionally comprise additives to meet various further demands. By way of example, in order to prevent contamination on the recording head during recording, an oil-absorbing substance such as inorganic pigment and polyurea filler may be dispersed in the binder. Further, in order to provide enhanced releasability from the recording head, an aliphatic acid, metallic soap, etc., may be added to the system. Thus, in general, an electron-providing colorless dye and an electron-accepting compound are directly used for color development. Besides these compounds, additives such as heat-fusible materials, pigments, wax, antistatic agents, light fastness improvers, ultraviolet absorbents, anti-foaming agents, conductance-providing agents, fluorescent dyes and surface active agents, are coated on the support to form the recording material of the present invention.

Further, a protective layer may be provided on the surface of the heat-sensitive recording material as necessary. The protective layer may be a laminate of two or more layers as necessary. In order to correct the curl balance of the support or enhance the chemical resistance on the back side of the recording material, a coating solution similar to the protective layer may be coated on the back side of the recording material. The recording material may be coated with an adhesive on the back side thereof in combination with a release paper to assume the form of label.

In general, the electron-providing colorless dye and the electron-accepting compound may be coated on the support in the form of dispersion in a binder the binder may be one commonly used a water-soluble binder. Examples of such a water-soluble binder include polyvinyl alcohol, hydroxyethyl cellulose, hydroxypropyl cellulose, epichlorohydrin-denatured polyamide, ethylenemaleic anhydride copolymer, styrene-maleic anhydride copolymer, isobutylene-maleic anhydride-salicylic acid copolymer, polyacrylic acid, amide polyacrylate, methylol-denatured polyacrylamide, starch derivative, casein, and gelatin.

In order to render these binders water resistant, a waterproofing agent or a hydrophilic polymer emulsion such as styrene-butadiene rubber latex and acrylic resin emulsion may be incorporated into these binders.

The heat-sensitive coating solution thus obtained is then coated on a high quality paper, a high quality paper having a subbing layer, a synthetic paper, a plastic film, etc. This support is particularly preferably one having a smoothness of 500 seconds or more, particularly 800 seconds or more, as specified in JIS-8119 from the standpoint of dot reproducibility.

In the case where a subbing layer comprising a pigment as a main component is provided on the support, this pigment may be any common organic or inorganic pigment. In particular, a pigment having an oil absorption of 40 cc/100 g or more as specified in JIS-K5101 may be preferably used. Specific examples of such a pigment include calcium carbonate, barium sulfate, titanium oxide, talc, agalmatolite, kaolin, calcined kaolin, aluminum hydroxide, amorphous silica, urea formaldehyde resin powder, and polyethylene resin powder.

If such a pigment is-coated on the support, the amount of the pigment is 2 g/m$^2$, preferably 4 g/m$^2$, or more.

Examples of the binder to be used for the subbing layer include water-soluble high molecular compounds and water-soluble binders. These binders may be used singly or in admixture.

Examples of such a water-soluble high molecular compounds include methyl cellulose, carboxymethyl cellulose, hydroxymethyl cellulose, starch, gelatin, gum arabic, casein, styrene-maleic anhydride copolymer hydrolyzate, ethylene-maleic anhydride copolymer hydrolyzate, polyvinyl alcohol, and polyacrylamide.

This water-soluble binder may normally be a synthetic rubber latex or synthetic resin emulsion. Examples of such a water-soluble binder include styrene-butadiene rubber latex, acrylonitrile-butadiene rubber latex, methyl acrylate-butadiene rubber latex, and vinyl acetate emulsion.

The amount of the binder to be used is normally 3 to 100% by weight, preferably 5 to 50% by weight, based on the weight of pigment. The subbing layer may comprise a wax, a decoloration inhibitor, a surface active agent, etc., incorporated therein.

Examples of pigments to be used as additives in the present invention include kaolin, calcined kaolin, talc, agalmatolite, diatomaceous earth, calcium carbonate, aluminum hydroxide, magnesium hydroxide, zinc oxide, lithopone, amorphous silica, colloidal silica, calcined gypsum, silica, magnesium carbonate, titanium oxide, alumina, barium carbonate, barium sulfate, mica, microballoon, urea-formalin filler, polyester particle, and cellulose filler.

Examples of the metallic soap include polyvalent metallic salts of higher aliphatic acids such as zinc stearate, aluminum stearate, calcium stearate and zinc stearate.

In the present invention, a wax having a melting point of 40° to 120° C. is preferably used in light of head matching with respect to facsimile.

Preferred examples of such a wax having a melting point of 40° to 120° C. include paraffin wax, polyethylene wax, carnauba wax, microcrystalline wax, candelilla wax, montan wax, and aliphatic amide wax. Particularly preferred examples of such a wax are paraffin wax, montan wax and methyl stearoamide having a melting point of 50° to 100° C.

The amount of the wax to be used is normally 5 to 200% by weight, preferably 20 to 150% by weight, based on the weight of electron-providing colorless dye.

For enhancement of light fastness, hindered phenol compounds may be used. Among these hindered phenol compounds, a phenol derivative in which at least one of the 2-position and the 6-position is substituted with a branched alkyl group, is preferred.

The ultraviolet absorbent to be used in the present invention may be cinnamic acid derivatives, benzophenone derivatives, benzotriazole phenol derivatives or the like. Examples of these ultraviolet absorbents include butyl α-cyano-β-phenylcinnamate, o-benzotriazole phenol, o-benzotriazole-p-chlorophenol, o-benzotriazole-2,4-di-t-butylphenol, and o-benzotriazolyl-2,4-di-t-octylphenol.

Examples of the waterproofing agent to be used in the present invention include water-soluble initial condensates such as N-methylolurea, N-methylmelamine and urea-formaldehyde, dialdehyde compounds such as glyoxal and glutaraldehyde, inorganic crosslinking agents such as boric acid and borax, and blend heat-treating agents such as polyacrylic acid, methylvinylether-maleic acid copolymer and isobutyrene-maleic anhydride copolymer.

Examples of materials to be used for the protective layer include water-soluble high molecular compounds such as polyvinyl alcohol, carboxy-denatured polyvinyl alcohol, vinyl acetate-acrylamide copolymer, silicon-denatured polyvinyl alcohol, starch, denatured starch, methyl cellulose, carboxymethyl cellulose, hydroxymethyl cellulose, gelatin, gum arabic, casein, styrene-maleic acid copolymer hydrolyzate, styrenemaleic acid copolymer half ester hydrolyzate, isobutyrene-maleic anhydride copolymer hydrolyzate, polyacrylamide derivative, polyvinyl pyrrolidone, sodium polystyrenesulfonate and sodium alginate, styrene-butadiene rubber latex, acrylonitrile-butadiene rubber latex, methyl acrylate-butadiene rubber latex, and vinyl acetate emulsion.

In order to enhance matchability with the heat-sensitive head, the protective layer may comprise a pigment, a metallic soap, a wax, a waterproofing agent, etc., incorporated therein.

When the protective layer is coated on the heat-sensitive coloring layer, a surface active agent may be incorporated into the coating solution to obtain a uniform protective layer. This surface active agent may be an alkaline metal salt of sulfosuccinic acid, a fluorine-containing surface active agent or the like. In particular, sodium salt or ammonium salt of di-(n-hexyl)sulfosuccinic acid, di-(2-ethylhexyl)-sulfosuccinic acid or the like may be preferably used. Among these surface active agents, anionic surface active agents exert appreciable effects.

If the recording material of the present invention is used as a pressure-sensitive paper, it may be in various forms as disclosed in U.S. Pat. Nos. 2,505,470, 2,505,471, 2,505,489, 2,548,366, 2,712,507, 2,730,456, 2,730,457, 3,103,404, 3,418,250, and 4,010,038. In the most general embodiment, the recording material comprises at least a pair of sheets which separately contain an electron-providing colorless dye and an electron-accepting compound.

The preparation of capsules can be accomplished by a method utilizing coacervation of hydrophilic colloidal sol as disclosed in British Patents 2,800,457, and 2,800,458, or a method as disclosed in British Patents 867,797, 950,443, 989,264, and 1,091,076.

In general, one or more electron-providing colorless dyes are dissolved in a solvent (e.g., synthetic oils such as alkylated naphthalene, alkylated diphenyl, alkylated diphenyl methane, alkylated terphenyl and chlorinated paraffin, vegetable oil such as cottonseed oil and castor oil, animal oil, mineral oil, mixture thereof), incorporated into microcapsules, and then coated on a paper, high quality paper, plastic sheet, resin-coated paper or the like, to prepare a coloring agent sheet.

Alternatively, an electron-accepting compound and optionally an additive or a mixture of additives are dispersed in a binder such as styrene-butadiene latex and polyvinyl alcohol, and then coated on a support such as paper, plastic sheet and resin-coated paper with a pigment to obtain a color developer sheet.

The binder is preferably a carboxy-denatured styrene-butadiene latex and a water-soluble high molecular compound in combination to achieve good light and water resistance. The pigment is preferably calcium carbonate having an average grain diameter of 5.0 μm or less in an amount of 60% by weight based on the total weight of pigment, in the light of color developability.

The amount of the electron-providing colorless dye and electron-accepting compound to be used depend on the desired thickness of the coat, the form of the pressure-sensitive recording paper, the process for the preparation of the capsules, and other conditions. Those skilled in the art can easily determine these values.

The present invention will be further described in the following examples, but the present invention should not be construed as being limited thereto. In these examples, the unit % indicates the percentage by weight unless otherwise specified.

EXAMPLE 1

Twenty g of 2-anilino-3-methyl-6-N-methyl-N-normalpropylaminofluoran as an electron-providing colorless dye, 20 g of Exemplary Compound (1) as an electron-accepting compound, and 20 g of 2-naphthylbenzylether as a heat-fusible material, were each dispersed with 10 g of a 5% aqueous solution of a polyvinyl alcohol (Kuraray PVA105) by means of a ball mill over 24 hours, to prepare grains having a volume-average grain diameter of 3 μm. On the other hand, 80 g of calcined kaolin (Anisilex-93) was dispersed with 160 g of a 0.5% aqueous solution of sodium hexametaphosphate by means of a homogenizer.

These dispersions thus obtained were then mixed in a proportion of 5 g of electron-providing colorless dye, 10 g of electron-accepting compound, 10 g of diaryloxy alkane compound dispersion and 22 g of calcined kaolin dispersion. To this mixture were then added 4 g of a zinc stearate emulsion and 5 g of a 2% aqueous solution of sodium (2-ethylhexyl)sulfosuccinate to prepare a coating solution. This coating solution was then coated on a high quality paper having a weight of 50 g/m² in an amount such that the dry coated amount reached 6 g/m² by means of a wire bar. The material was then calendered to obtain a coated paper.

The coated paper thus obtained was then subjected to typing of pulse with a width of 1.0 by means of a heat-sensitive typing experimental apparatus equipped with a thermal head (KLT-216-8MPD1 available from Kyocera) and a 100 kg/cm$^2$ pressure roll disposed shortly before the thermal head under the conditions of a head voltage of 24 V and a pulse cycle of 10 ms. The type density was measured by a Macbeth reflection densitometer RD-918. The color density was 1.38.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

EXAMPLE 2

A coated paper was prepared in the same manner as in Example 1, except that Exemplary Compound (1) used as an electron-accepting compound was replaced by Exemplary Compound (2). The coated paper specimen was subjected to color development in the same manner as in Example 1. As a result, the color density was 1.35.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

EXAMPLE 3

A coated paper was prepared in the same manner as in Example 1, except that Exemplary Compound (1) used as an electron-accepting compound was replaced by Exemplary Compound (3). The coated paper specimen was subjected to color development in the same manner as in Example 1. As a result, the color density was 1.36.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

EXAMPLE 4

A coated paper was prepared in the same manner as in Example 1, except that Exemplary Compound (1) used as an electron-accepting compound was replaced by Exemplary Compound (17). The coated paper specimen was subjected to color development in the same manner as in Example 1. As a result, the color density was 1.34.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

EXAMPLE 5

A coated paper was prepared in the same manner as in Example 1, except that Exemplary Compound (1) used as an electron-accepting compound was replaced by Exemplary Compound (13). The coated paper specimen was subjected to color development in the same manner as in Example 1. As a result, the color density was 1.34.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

EXAMPLE 6

A coated paper was prepared in the same manner as in Example 1, except that Exemplary Compound (1) used as an electron-accepting compound was replaced by Exemplary Compound (25). The coated paper specimen was subjected to color development in the same manner as in Example 1. As a result, the color density was 1.33.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the image the background and no discoloration on the portion.

EXAMPLE 7

A coated paper was prepared in the same manner as in Example 1, except that Exemplary Compound (1) used as an electron-accepting compound was replaced by Exemplary Compound (20). The coated paper specimen was subjected to color development in the same manner as in Example 1. As a result, the color density was 1.32.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

EXAMPLE 8

A coated paper was prepared in the same manner as in Example 1, except that Exemplary Compound (1) used as an electron-accepting compound was replaced by Exemplary Compound (21). The coated paper specimen was subjected to color development in the same manner as in Example 1. As a result, the color density was 1.33.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

EXAMPLE 9

A coated paper was prepared in the same manner as in Example 1, except that 2-anilino-3-methyl-6-N-methyl-N-normalpropylaminofluoran used as an electron-providing compound was replaced by 2-anilino-3-methyl-6-N-dibutylaminofluoran as an electron-providing compound. The coated paper specimen was subjected to color development in the same manner as in Example 1. As a result, the color density was 1.32.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

EXAMPLE 10

1) Preparation of an electron-providing colorless dye-containing capsule sheet

Five parts of a partial sodium salt of a polyvinyl benzenesulfonic acid (VERSA, TL500 available from National Starch) was dissolved in 95 parts of water. To the solution was added an aqueous solution of sodium hydroxide to make pH 4.0. On the other hand, 100 parts of diisopropylnaphthalene having 2-anilino-3-methyl-6-N-methyl-N-normalpropylaminofluoran as an electron-providing colorless dye in an amount of 4.5% were emulsion-dispersed in 100 parts of the aforementioned 5% aqueous solution of a partial sodium salt of a polyvinylbenzenesulfonic acid to obtain an emulsion of grains having a grain diameter of 4.0 $\mu$m.

Separately, 6 parts of melamine, 11 parts of a 37% aqueous solution of formaldehyde, and 30 parts of water were heated to a temperature of 60° C. with stirring to obtain a transparent aqueous solution of initial melamineformaldehyde polymer. The aqueous solution was mixed with the aforementioned emulsion. The solution was then adjusted with an aqueous solution of phosphoric acid with stirring to a pH of 6.0. The solution was then stirred at an elevated temperature of 65° C. for 6 hours. The capsule solution was then cooled to room temperature. The capsule solution was then adjusted with an aqueous solution of sodium hydroxide to a pH of 9.0.

To the dispersion thus prepared were then added 200 parts of a 10% aqueous solution of a polyvinyl alcohol and 50 parts of starch grains. Water was then added to the solution to prepare a solution of micro-capsule dispersion having a solid content concentration of 20%.

The solution was coated on a paper having a weight of 50 g/m$^2$ in an amount of 5 g/m$^2$ calculated in terms of solid content by means of an air knife coater, and then dried to obtain an electron-providing colorless dye-containing capsule sheet.

2) Preparation of an electron-accepting compound sheet

Fourteen parts of Exemplary Compound (17), 80 parts of calcium carbonate, 20 parts of zinc oxide and 1 part of sodium hexametaphosphate were added to 200 parts of water and dispersed therein by means of a sand grinder to make the solid contents have an average grain diameter of 3 $\mu$m. To the dispersion were then added 100 parts of a 10% aqueous solution of PVA and 10 parts (as calculated in terms of solid content) of a carboxyde-natured SBR latex. Water was then added to the dispersion in an amount such that the solid content concentration reached 20% to obtain a coating solution. The coating solution thus obtained was coated on a paper having a weight of 50 g/m$^2$ in an amount of 5.0 g/m$^2$ calculated in terms of solid content by means of an air knife coater, and then dried to obtain an electron-accepting compound sheet.

The electron-providing colorless dye-containing capsule sheet was then laminated with the electron-accepting compound sheet in such a manner that the capsule sheet side was brought into contact with the electron-accepting compound sheet. The recording material thus obtained was then subjected to color development under a load of 400 kg/cm$^2$. The color hue was a strong black. Portions which had been color-developed to black with a fluorescent pen or the like on the image portion were not decolored. The specimen also showed other excellent resistances (e.g., weathering resistance, plasticizer resistance).

EXAMPLE 11

A coated paper was prepared in the same manner as in Example 4, except that Exemplary Compound (17) (melting point: 195° to 196° C.) used as an electron-accepting compound was replaced by Exemplary Compound (17) having water of crystallization (melting point: 100° C.). The coated paper specimen was subjected to color development in the same manner as in Example 10. As a result, the color density was 1.24.

Portions which had been color-developed to black with a fluorescent pen or the like on the image portion were not decolored. Further, the white background was not color-developed to black (fog with solvent).

The coated paper specimen also showed other excellent resistances (e.g., weathering resistance, plasticizer resistance) and no fog and discoloration on the background and no discoloration on the image portion.

Comparative Example 1

A coated paper was prepared in the same manner as in Example 1, except that Exemplary Compound (1) used as an electron-accepting compound was replaced by 1,3-bis(4-hydroxyphenylsulfonylmethyl)benzene. The coated paper specimen was then subjected to color development in the same manner as in Example 1. As a result, the color density was 1.33.

The coated paper specimen was then painted with a fluorescent pen in the same manner as in Example 1. As a result, portions which had been color-developed to black with the fluorescent pen on the image portion were not decolored. However, the white background was heavily color-developed to black, showing fog with solvent.

Comparative Example 2

A coated paper was prepared in the same manner as in Example 1, except that Exemplary Compound (1) used as an electron-accepting compound was replaced by 1,3-bis[3-(4-hydroxyphenylsulfonyl)propoxy]benzene. The coated paper specimen was then subjected to color development in the same manner as in Example 1. As a result, the color density was 1.35.

The coated paper specimen was then painted with a fluorescent pen in the same manner as in Example 1. As a result, portions which had been color-developed to black with the fluorescent pen on the image porton were decolored. Further, the white background was heavily color-developed to black, showing fog with solvent.

EXAMPLE 12

Synthesis of Exemplary Compound (17) having two water molecules 18.4 g of 4-chlorosulfonyl diphenyl ether and 1.2 g of ferric chloride were added to 30 ml of chlorobenzene. The mixture was stirred at a temperature of 130° C. for 24 hours. After cooling, 20 ml of dimethyl sulfoxide was added to the solution. Chlorobenzene was then distilled off at a temperature of 170° C. 20 ml of dimethyl sulfoxide and 50 g of a 48% sodium hydroxide were then added to the solution. The solution was then heated under reflux for 24 hours. The mixture was then poured into water. The solution was then neutralized with hydrochloric acid. The solid content was then filtered off. The solid content was then dissolved in a 1:1 solution of toluene and ethyl acetate. The solution was then heated under reflux. The upper layer was separated from the lower layer. The solvent was then removed from the upper layer. The material was then recrystallized from a mixture of water and acetic acid to obtain a product. (m.p. 100°–102° C.)

EXAMPLE 13

Preparation of Exemplary Compound (17) in glassy form

The compound obtained in Example 1 was heated to a temperature of 130° C. to remove water of crystallization. The material was then cooled to room temperature to obtain a transparent glassy substance. The substance did not exhibit any melting point. The following spectral data proved that the substance was Exemplary Compound (17).

$^1$H-NMR (400 MHz, Aceton/TMS) data 9.45 ppm (s, 2H), 7.92 ppm (d, 4H), 7.78 ppm (d, 4H), 7.28 ppm (d, 4H), 6.95 ppm (d, 4H) MS (m/e) data 482 (M+), 417, 373, 342, 326, 28

EXAMPLE 14

Synthesis of Exemplary Compound (1)

Exemplary Compound (1) was prepared in the same manner as in Example 12, except that 4-chlorosulfonyl diphenyl ether was replaced by bis-4,4'-chlorosulfonyl biphenyl. (m.p. 240°–242° C.)

EXAMPLE 15

Synthesis of Exemplary Compound (25)

Exemplary Compound (25) was prepared in the same manner as in Example 12, except that 4-chlorosulfonyl diphenyl ether was replaced by bis-1,5-chlorosulfonyl naphthalene. (m.p. 300° C. or higher)

EXAMPLE 16

Synthesis Of Exemplary Compound (13)

Exemplary Compound (13) was prepared in the same manner as in Example 12, except that 4-chlorosulfonyl diphenyl ether was replaced by bis-2,7-chlorosulfonyl naphthalene. (m.p. 285°–295° C.)

EXAMPLE 17

Synthesis of Exemplary Compound (2)

6.5 g of Exemplary Compound (1), 1.55 g of a 48% aqueous solution of NaOH, 40 ml of methanol, and 2.64 g of amyl bromide were charged into a 200-ml flask, and then heated to a temperature of 80° C. with stirring for 3 hours. The reaction mixture was poured into iced-water. The material was then extracted with ethyl acetate. The extract was then purified through a column chromatography (developing solvent: 2:1 mixture of hexane and ethyl acetate) to isolate the product. (m.p. 187° C.)

The results of the examples show that the recording material of the present invention exhibits a high sensitivity and excellent weathering resistance and chemical resistance.

While the invention has been described in detail and with reference to specific embodiments thereof, it will be apparent to one skilled in the art that various changes and modifications can be made therein without departing from the spirit and scope thereof.

What is claimed is:

1. A recording material comprising an electron-providing colorless dye and an electron-accepting compound comprising an electron-accepting compound represented by the following formula (1):

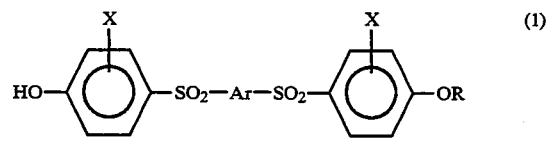

wherein X represents a hydrogen atom, a halogen atom, a hydroxyl group, a carboxyl group, an alkoxycarbonyl group, an alkyl group, an alkoxy group, an allyl group, an aryl group, an aralkyl group or a cycloalkyl group; Ar represents an arylene group containing two to five benzene rings, an arylene group condensed with two to five benzene rings or a bisarylene group in which arylene groups are connected to each other via a divalent group; and R represents a hydrogen atom, an alkyl group, an aralkyl group or an aryloxyalkyl group.

2. The recording material according to claim 1, wherein said electron-accepting compound is a diphenylether derivative represented by the following formula (2):

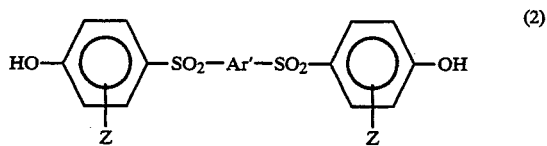

wherein Ar' is an arylene group containing two to five benzene rings, an arylene group condensed with two to five benzene rings, or a bisarylene group in which arylene groups are connected to each other via a divalent group; and Z represents a hydrogen atom, a halogen atom, an alkyl group, an aralkyl group, an allyl group, an aryl group, a hydroxyl group, a carboxyl group, an alkoxy group or an alkoxycarbonyl group.

3. The recording material according to claim 2, wherein said electron-accepting compound is a diphenylether derivative represented by the following formula (3):

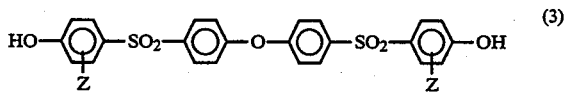

wherein Z is as defined in claim 2.

4. The recording material according to claim 3, wherein the compound represented by formula (3) is a diphenylether compound in which Z is a hydrogen atom, a halogen atom, a $C_{1-10}$ alkyl group, a $C_{6-10}$ aralkyl group, a $C_{6-10}$ aryl group or an allyl group.

5. The recording material according to claim 1, wherein the compound represented by formula (1) is in the form of a crystal containing water.

6. The recording material according to claim 1, wherein the compound represented by formula (1) is in the form of a crystal containing an organic solvent.

* * * * *